United States Patent [19]

Schwalley et al.

[11] 4,124,520

[45] Nov. 7, 1978

[54] ANTI-MICROBIAL BATHROOM CLEANING COMPOSITIONS CONTAINING O-BENZYL-4-CHLOROPHENOL

[75] Inventors: Lawrence L. Schwalley, Whittier; Donald J. Ferm, Fullerton, both of Calif.

[73] Assignee: United States Borax & Chemical Corp., Los Angeles, Calif.

[21] Appl. No.: 807,774

[22] Filed: Jun. 20, 1977

[51] Int. Cl.$^2$ ................ A61K 31/055; A61K 31/085; A61L 13/00; C11D 3/48

[52] U.S. Cl. .................................... 252/106; 252/153; 252/173; 252/DIG. 14; 424/340; 424/347

[58] Field of Search ............... 252/106, 550, 558, 546, 252/153, 173, DIG. 14; 424/340, 347

[56] References Cited

U.S. PATENT DOCUMENTS

| | | | |
|---|---|---|---|
| 2,317,505 | 4/1943 | Wassell | 252/161 |
| 3,002,883 | 10/1961 | Butt et al. | 252/106 |
| 3,824,190 | 7/1974 | Winicov et al. | 252/106 |
| 3,897,357 | 7/1975 | Carmello et al. | 252/106 |
| 3,933,671 | 1/1976 | Heile | 252/106 |
| 3,965,520 | 6/1976 | Maier | 252/106 |

FOREIGN PATENT DOCUMENTS

| | | | |
|---|---|---|---|
| 858,030 | 1/1961 | United Kingdom | 424/347 |

OTHER PUBLICATIONS

McCutcheon's Detergents and Emulsifiers - 1970 Annual, published by Allured Publishing Co., Ridgewood, N.J. pp. 10-24.

McCutcheon's Detergents and Emulsifiers 1972 Annual, Allured Publishing Corporation, Ridgewood, N.J., (1972).

*Primary Examiner*—Dennis L. Albrecht

*Attorney, Agent, or Firm*—James R. Thornton

[57] ABSTRACT

Aqueous solutions containing o-benzyl-4-chlorophenol, tetrasodium ethylenediamine tetraacetate or trisodium nitrilotriacetate, sodium 2-ethylhexyl sulfate and glycol solvent. The solutions are antimicrobial cleaning compositions especially useful for the bathroom.

11 Claims, No Drawings

ANTI-MICROBIAL BATHROOM CLEANING COMPOSITIONS CONTAINING O-BENZYL-4-CHLOROPHENOL

RELATED APPLICATION

Schwalley application Ser. No. 745,520 filed Nov. 26, 1976, now abandoned, describes and claims an antimicrobial bathroom cleaning composition containing 5-chloro-2-(2,4-dichlorophenoxy)-phenol.

This invention relates to antimicrobial solutions, and more particularly to antimicrobial aqueous solutions useful as bathroom cleaner compositions.

One of the more difficult areas of the home to clean is the bathroom where a useful cleaner should not only be effective in removing unsightly soap scum, but should also be germicidal for use in and around the shower, toilet bowl and wash basin.

The present invention provides an aqueous solution having superior properties for removing soap scum and also for killing fungi, such as athlete's foot fungus, mildew and black mold as well as numerous germs. Thus, the present compositions are useful in cleaning, deodorizing and disinfecting bathroom showers, toilet bowls and wash basins.

The aqueous solutions of this invention contain four necessary ingredients in specific amounts. Such solutions comprise, by weight, about 0.05 to 0.5% of o-benzyl-4-chlorophenol, about 2 to 15% of trisodium nitrilotriacetate or tetrasodium ethylenediamine tetraacetate, about 0.5 to 4% of sodium 2-ethylhexylsulfate and about 0.5 to 12% of a water-miscible glycol solvent.

The o-benzyl-4-chlorophenol is commercially available under the trademark SANTOPHEN-1. Sodium 2-ethylhexyl sulfate is also commercially available under the trademark TERGITOL 08. The water-miscible glycol solvent is preferably hexylene glycol (2-methylpentane-2,4-diol) or a polyethylene glycol of the formula $HO(CH_2CH_2O)_n$—H, having a molecular weight of up to about 600. These polyethylene glycols are commercially available under the trademarks, Carbowax 200, Carbowax 400 and Carbowax 600, in which 200, 400 and 600 indicate the average molecular weight of the compound.

The aqueous solutions preferably also contain minor amounts of other beneficial components such as the lower alkanols, ethyl and isopropyl alcohol, which are included as co-solvents and to enhance antimicrobial activity. Other surfactants may also be present, such as about 0.1 to 0.4% of sodium dodecylbenzene sulfonate which is added as the acid. Further, it is preferred that the pH of the solution be in the range of about 10.0 to 10.5, and a small amount of acid such as acetic acid, or base such as sodium hydroxide, may be added for pH control. Also, small amounts of perfume and dye may be included, if desired.

A preferred composition, according to this invention, contains about 0.06 to 0.2% of the o-benzyl-4-chlorophenol, about 3 to 10% of the tetrasodium ethylenediamine tetraacetate, about 1 to 2% of the sodium 2-ethylhexyl sulfate, about 1 to 10% of the glycol solvent which is preferably hexylene glycol, and about 2 to 5% isopropyl alcohol. Such preferred solutions have a pH of about 10.3, adjusted by addition of acid or base.

The compositions of this invention can be used to clean and disinfect hard surfaces in the bathroom, such as fiberglass and porcelain showers and tubs, stainless steel, grouting, chrome, enamel woodwook and vanity tops. In using the compositions, they are merely sprayed onto the surface to be cleaned, allowing sufficient time to wet the surface thoroughly. The surface is then wiped with a damp cloth or sponge or rinsed off with water. If the surface is heavily soiled, it is preferred to allow about 2 to 5 minutes for the spray to penetrate and then use a non-scratching pad or brush before rinsing. Unsightly hard water dirt and soap scum are readily removed and the cleaned surface is disinfected. The compositions will kill germs and fungi such as *Staphylococcus aureus, Salmonella choleraesius, Pseudomonas aeruginosa, Mycobacterium tuberculosis, Escherichia coli, Streptococcus pyogenes, Enterbacter aerogenes, proteus mirabilis,* athlete's foot fungus (*Trycophyton mentagrophytes*), *Candida albicans,* and black mold such as *Aspergillus niger.*

The following are representative examples of the antimicrobial compositions of this invention.

EXAMPLE 1

| | % by weight |
|---|---|
| hexylene glycol | 1.0 |
| o-benzyl-4-chlorophenol | 0.15 |
| sodium 2-ethylhexyl sulfate (40% active) | 4.5 |
| dodecylbenzene sulfonic acid | 0.3 |
| tetrasodium EDTA (38% active) | 12.5 |
| isopropyl alcohol | 2.5 |
| sodium hydroxide | 0.0126 |
| perfume | 0.08 |
| water | balance |

EXAMPLE 2

| | |
|---|---|
| hexylene glycol | 1.0 |
| o-benzyl-4-chlorophenol | 0.15 |
| sodium 2-ethylhexyl sulfate (40%) | 4.5 |
| trisodium NTA-$H_2O$ | 6.86 |
| isopropyl alcohol | 2.5 |
| dodecylbenzene sulfonic acid | 0.3 |
| perfume | 0.08 |
| sodium hydroxide | Q.S.* to pH 10.3 |
| water | balance |

*quantity sufficient

EXAMPLE 3

| | % by weight |
|---|---|
| Carbowax 400 | 10.0 |
| o-benzyl-4-chlorophenol | 0.2 |
| sodium 2-ethylhexyl sulfate (40%) | 4.5 |
| tetrasodium EDTA (38%) | 25.0 |
| isopropyl alcohol | 5.0 |
| acetic acid | Q.S.* to pH 10.3 |
| perfume | 0.08 |
| water | balance |

EXAMPLE 4

| | |
|---|---|
| hexylene glycol | 2.5 |
| o-benzyl-4-chlorophenol | 0.15 |
| sodium 2-ethylhexyl sulfate (40%) | 4.5 |
| tetrasodium EDTA (38%) | 12.5 |
| dodecylbenzene sulfonic acid | 0.3 |
| isopropyl alcohol | 2.5 |
| sodium hydroxide | Q.S.* to pH 10.3 |
| perfume | 0.8 |
| water (distilled) | balance |

*quantity sufficient

EXAMPLE 5

| | % by weight |
|---|---|
| hexylene glycol | 7.5 |
| o-benzyl-4-chlorophenol | 0.15 |
| sodium 2-ethylhexyl sulfate (40%) | 4.5 |
| tetrasodium EDTA (38%) | 12.5 |
| dodecylbenzene sulfonic acid | 0.3 |
| isopropyl alcohol | 2.5 |
| perfume | 0.08 |
| sodium hydroxide | Q.S.* to pH 10.3 |
| water (distilled) | balance |

The compositions of Examples 1 and 2 were tested by standard procedures in order to determine their efficacy in killing various germs and fungi following the procedure described in the *Official Methods for Analysis of the AOAC*, 11th Edition, 1970, Chapter 4, paragraph 4.003 - 4.035, "Spray Disinfectant Test". Also, the Environmental Protection Agency's "Hard Surface Mildew Fungistatic Test Method" (Revised 12-1-70) was used to test the effectiveness of the compositions against Aspergillus niger. The following results were obtained.

Test Results

| Organism | Ex. 1 | Ex. 2 |
|---|---|---|
| *Staphylococcus a.* (30C) | 0/0 | 0/0 |
| *Salmonella c.* (20C) | 0/0 | — |
| (30C) | — | 0/0 |
| *Pseudomonas a.* (30C) | 0/0 | — |
| *Aspergillus n.* (4 weeks) | 0 | — |

The first figure in the test results indicates the number of culture tubes found with live growing organisms in the initial test, while the second figure indicates the number of live cultures found in the secondary, or subculture tests.

Various changes and modifications of the invention can be made, and, to the extent that such variations incorporate the spirit of this invention, they are intended to be included within the scope of the appended claims.

What is claimed is:

1. An anti-microbial aqueous solution consisting essentially of water and, by weight, about 0.05 to 0.5% of o-benzyl-4-chlorophenol, about 2 to 15% tetrasodium ethylenediamine tetraacetate or trisodium nitrilotriacetate, about 0.5 to 4% of sodium 2-ethylhexyl sulfate, about 2 to 5% of lower alkanol and about 0.5 to 12% of water-miscible glycol solvent selected from the group consisting of hexylene glycol and polyethylene glycols having a molecular weight of up to about 600.

2. A solution in accordance with claim 1 in which about 1 to 10% hexylene glycol is included as said glycol solvent.

3. A solution in accordance with claim 1 in which said water-miscible glycol solvent is hexylene glycol.

4. A solution in accordance with claim 1 in which about 0.1 to 0.4% of sodium dodecylbenzene sulfonate is included.

5. An aqueous solution in accordance with claim 1 in which said lower alkanol is isopropanol.

6. An aqueous solution in accordance with claim 1, consisting essentially of water, about 0.06 to 0.2% of said o-benzyl-4-chlorophenol, about 3 to 10% of said tetrasodium ethylenediamine tetraacetate, about 1 to 2% of said sodium 2-ethylhexyl sulfate, about 1 to 10% of said water-miscible glycol solvent and about 2 to 5% of isopropyl alcohol.

7. An aqueous solution in accordance with claim 6 in which said water-miscible glycol solvent is hexylene glycol.

8. An aqueous solution in accordance with claim 6 including about 0.3% of dodecylbenzene sulfonic acid.

9. An aqueous solution in accordance with claim 1 having a pH of about 10.0 to 10.5.

10. An aqueous solution according to claim 6 having the composition

| | |
|---|---|
| hexylene glycol | 1.0% |
| o-benzyl-4-chlorophenol | 0.15% |
| sodium 2-ethylhexyl sulfate | 1.8% |
| dodecylbenzene sulfonic acid | 0.3% |
| tetrasodium EDTA | 4.75% |
| isopropyl alcohol | 2.5% |
| sodium hydroxide | 0.0126% |
| perfume and water | balance |

said % being per cent by weight.

11. An aqueous solution according to claim 6 having the composition

| | |
|---|---|
| hexylene glycol | 1.0% |
| o-benzyl-4-chlorophenol | 0.15% |
| sodium 2-ethylhexyl sulfate | 1.8% |
| trisodium NTA.$H_2O$ | 6.86% |
| isopropyl alcohol | 2.5% |
| dodecylbenzene sulfonic acid | 0.3% |
| sodium hydroxide | Q.S. to pH 10.3 |
| perfume and water | balance |

wherein said Q.S. is quantity sufficient and said % is per cent by weight.

* * * * *